United States Patent [19]
Deisher

[11] Patent Number: 5,929,058
[45] Date of Patent: Jul. 27, 1999

[54] TREATMENT AGENTS AND METHODS FOR TREATING TYPE II DIABETES AND SYMPTOMS OF TYPE II DIABETES

[75] Inventor: Theresa A. Deisher, Seattle, Wash.

[73] Assignee: Zymogenetics, Inc., Seattle, Wash.

[21] Appl. No.: 08/995,739

[22] Filed: Dec. 19, 1997

Related U.S. Application Data

[60] Provisional application No. 60/034,505, Dec. 24, 1996.

[51] Int. Cl.$^6$ .......................... A61K 31/58; A61K 31/56; A61K 31/00
[52] U.S. Cl. ......................... 514/169; 514/170; 514/171
[58] Field of Search ................................... 514/169, 170, 514/171

[56] References Cited

U.S. PATENT DOCUMENTS

| | | |
|---|---|---|
| 4,981,784 | 1/1991 | Evans et al. . |
| 5,217,867 | 6/1993 | Evans et al. . |
| 5,232,917 | 8/1993 | Bolger et al. . |
| 5,262,300 | 11/1993 | Evans et al. . |
| 5,310,662 | 5/1994 | Evans et al. . |

FOREIGN PATENT DOCUMENTS

| | | | |
|---|---|---|---|
| 9218132 | 10/1992 | WIPO | ............................ A61K 31/58 |
| 9322685 | 11/1993 | WIPO | ............................ G01N 33/74 |
| 9518865 | 7/1995 | WIPO | ............................. C12Q 1/00 |
| 9531901 | 11/1995 | WIPO | ............................ A01N 31/00 |
| 9619458 | 6/1996 | WIPO | ......................... C07D 215/06 |
| 9636230 | 11/1996 | WIPO | ............................ A61K 31/56 |

OTHER PUBLICATIONS

Database Chemical Abstracts on STN, AN 1995:396499, Kornel et al, "Aldosterone increases transmembrane influx of Na+ in vascular smooth muscle cells through increased synthesis of Na Channels", Steroids, (1995), 60(1), 114–19, Jan. 1995.

Santiago M. Valle, et al., Further Studies in Deoxycorticosterone Acetate Treated Rats: Brain Content of Mineralocorticoid and Glucocorticoid Receptors and Effect of Steroid Antagonists on Salt Intake, *Neuroendocrinology*, 61: 117–124, 1995.

Atsuhisa Sata et al., High Glucose Stimulates Aldosterone–Induced Hyertrophy via Type I Mineralocortoid Receptors in Neonatal Rat Cardiomyocytes, *Endocrinology* 137(10): 4145–4153, 1996.

Mary F. Dallman et al., Feast and Famine: Critical Role of Glucocorticoids with Insulin in Daily Energy Flow, *Frontiers in Neuroendocrinology*, 14(4): 303–347, 1993.

DN Brindley, Role of glucocorticoids and fatty acids in the impairment of lipid metabolism observed in the metabolic syndrome, *International Journal of Obesity* 19(1), S69–S75, 1995.

Stuart Chalew et al., The Hypothalamic–Pituitary–Adrenal Axis in Obesity, Obesity Research 3(4), 371–382, 1995.

Chen et al., Type II glucocorticoid receptors in the CNS regulate metabolism in ob/ob mice independent of protein synthesis, Dept.of Food Science & Human Nutrition, Michigan State Univ., E427–432, 1994.

A. F. Debons et al., Gold Thiglucose–Induced Hypothalamic Damage, Hyperphagia, and Obesity: Dependence on the Adrenal Gland, *Endocrinology* 110(6): 2024–2029.

Craig C. Smith, Differential Mineralocorticoid (Type 1) and Glucocorticoid (Type 2) Receptor Expression in Lewis and Fischer Rats, *Neuroimmunomodulation I*: 66–73, 1994.

Chen et al., A Single Intracerebroventricular Injection of Dexamethasone Elevates Food Intake and Plasma Insulin and Depresses Metabolic Rates in Adrenalectomized Obese (ob/ob) Mice $^{1,2}$, Dept. of Food Science and Human Nutrition, Michigan State University, 540–545, 1994.

Saito et al., Adrenalectomy and food restriction in the genetically obese (ob/ob) mouse. *Am. J. Physiol.* 246: R–20–R25, 1984.

George A. Bray, Food Intake, Sympathetic Activity, and Adrenal Steroids, *Brain Research Bulletin* 32, pp. 537–541, 1993.

*Primary Examiner*—Keith D. MacMillan
*Attorney, Agent, or Firm*—Ann W. Speckman; Janet Sleath

[57] ABSTRACT

Methods for treating non-insulin dependent Diabetes Mellitus (NIDDM), or Type II Diabetes, by administering a combination of treatment agents exhibiting glucocorticoid receptor type I agonist activity and glucocorticoid receptor type II antagonist activity are disclosed. Treatment agents having both glucocorticoid receptor type I agonist activity and glucocorticoid receptor type II antagonist activity are also disclosed. Screening methods for identifying compounds having both glucocorticoid receptor type I agonist activity and glucocorticoid receptor type II antagonist activity are disclosed.

13 Claims, No Drawings

TREATMENT AGENTS AND METHODS FOR TREATING TYPE II DIABETES AND SYMPTOMS OF TYPE II DIABETES

REFERENCE TO PRIORITY APPLICATION

This application claims priority from U.S. Provisional Patent Application No. 60/034,505 filed Dec. 24, 1996, entitled Treatment Agents and Methods for Treating Type II Diabetes and Symptoms of Type II Diabetes.

FIELD OF THE INVENTION

The present invention relates to methods and agents for treating mammals suffering from non-insulin dependent Diabetes Mellitus ("NIDDM"), also referred to as Type II Diabetes, as well as symptoms of Type II Diabetes and Syndrome X, including hypertension, obesity, inadequate glucose clearance, hyperglycemia, hyperinsulinemia, hypertriglyceridemia, high circulating glucocorticoid levels, and the like. Suitable treatment agents exhibit specified glucocorticoid receptor agonist and/or antagonist activities, and treatment agents having such properties are disclosed. Screening methods for identifying treatment agents having the desired properties are also disclosed.

BACKGROUND OF THE INVENTION

Non-insulin-dependent Diabetes Mellitus ("NIDDM"), also known as Type II diabetes, is a debilitating disease characterized by high circulating blood glucose, insulin and corticosteroid levels. Increased hepatic glucose production, or gluconeogenesis, is the primary factor responsible for loss of glycemic control and leads to hyperglycemia and hyperinsulinemia. In individuals having Type II diabetes, excess glucose production occurs in spite of the availability of insulin, and circulating glucose levels remain excessively high as a result of inadequate glucose clearance. Syndrome X is a condition characterized by many of the same symptoms, and is generally a reliable early indicator of the development of Type II Diabetes.

The adrenal cortex synthesizes and releases three classes of steroid hormones: glucocorticoids; the sex steroids; and mineralocorticoids. Secretion of glucocorticoids and mineralocorticoids is known to follow a circadian pattern. The adrenal cortical hormones are lipid-soluble and readily pass through cell membranes of target tissues into the cytoplasm, where they combine with specific intracellular receptor proteins. Hormone-receptor complexes are translocated to the nucleus, where they bind to a glucocorticoid response element (GRE), which selectively activates or represses transcription from specific promoters.

In particular, glucocorticoids regulate the transcription of a number of genes which regulate gluconeogenesis, particularly PEPCK (Friedman et al., (1993), J. Biol. Chem., V268, p12952). PEPCK catalyzes the conversion of oxaloacetate to phosphoenolpyruvate and is considered a key regulatory step in gluconeogenesis. PEPCK activity and corresponding mRNA levels are elevated in NIDDM models. Unlike many enzymes in regulatory metabolic pathways, PEPCK is regulated primarily by hormonally induced changes in gene transcription.

Cortisol is the most important human glucocorticoid, and is synthesized endogenously through a series of reactions resulting in the conversion of cholesterol to cortisol. The comparable rodent glucocorticoid is corticosterone. Cortisol promotes gluconeogenesis and glycogen deposition in the liver, increases blood glucose levels, and decreases peripheral utilization of glucose. It also stimulates utilization of fatty acids and ketogenesis and has weak mineralocorticoid activity. Mineralocorticoids promote the retention of $Na^+$ and the loss of $K^+$ by the kidneys and thus assist in maintaining water and salt balances in the body. The major mineralocorticoid is aldosterone, which also has weak glucocorticoid activity.

Glucocorticoid receptors belong to a large super-family of ligand-dependent transcription factors that play diverse roles in homeostasis, growth and development. Two types of intracellular receptors bind corticosteroids with high affinity: glucocorticoid receptor type I, also referred to as mineralocorticoid receptor ("MR"); and glucocorticoid receptor type II, also referred to as glucocorticoid receptor ("GR"). Both the type I and type II receptors are activated by the same endogenous ligands and, in some cases, may regulate expression of the same genes. The type I receptor binds aldosterone and corticosterone with approximately equal affinity, and dexamethasone with lower affinity. The type II receptor binds dexamethasone with high affinity, and aldosterone and corticosterone with lower affinity. Coexpression of the enzyme 11-β hydroxysteroid dehydrogenase with the type I receptor metabolizes cortisol to its inactive form, cortisone, ensuring that the mineralocorticoids preferentially occupy the receptor. 11-β hydroxysteroid dehydrogenase is not present in the central nervous system, and glucocorticoids consequently bind to the type I receptor with high affinity in the central nervous system.

Type I and type II glucocorticoid receptors are found both centrally and peripherally. Type II receptor expression is moderate in the cerebral cortex, amygdala, thalamnus and hypothalamus, and abundant in the septum and hippocampus. The type I receptor has a limited distribution with moderate to high levels in the septal area and hippocainpus. Peripherally, type II receptors are expressed predominantly by adipose and liver cells, while Type I receptors are not normally accessible to glucocorticoid binding.

Certain functional domains within the receptor molecules have been identified that are thought to be responsible for DNA binding, hormone binding, and nuclear localization. The ligand binding domain has the ability to block activity of the receptor in the absence of hormone and thus, presence of the requisite hormone relieves the inhibition of the receptor to activity. Numerous hormone and hormone-like receptors have been isolated, identified, characterized and prepared.

Glucocorticoids are known to play an important role in the development and maintenance of obesity. The importance of glucocorticoids in glycemic control was established by showing that adrenalectomized diabetic mice returned to normal glycemia. Glucocorticoids are generally thought to play a permissive role by enhancing the availability of gluconeogenic substrates and increasing the sensitivity of the liver to the actions of glucagon and catecholamines.

Several studies have implicated the type II glucocorticoid receptor in the obese phenotype. A study using adrenalectomized gold thioglucose (GTG)-obese mice demonstrated that icv administration of the selective type II glucocorticoid agonist dexamethasone restored the obese phenotype, while type I agonism in contrast, using icv administration of desoxycorticosterone, lead to exasperated weight loss and eventually to death. A. F. Debons et al. "Gold thioglucose-induced hypothalamic damage, hyperphagia, and obesity: dependence on the adrenal gland"; Endocrinology 110:2024–2029, (1982). Another study demonstrated that icv administration of dexamethasone reduced thermogenesis in adrenalectomized ob/ob mice, while icv administration of aldosterone (a selective type I agonist) was without effect on thermogenesis. Chen, H. L. and Romsos, D. R., "Type II glucocorticoid receptors in the CNS regulate metabolism in ob/ob mice independent of protein synthesis," Am. J. Physiol. 1994 Mar;266 (3 Pt. 1): E427-32. Yet another study involved treating adrenalectomized ob/ob mice with either cortisone or desoxycortisone and demonstrated that only cortisone reduced lean muscle weight, while also increasing food intake and adipose weight. M. Saito and G. F. Bray, "Adrenalectomy and food restriction in the genetically obese (ob/ob) mouse," Am. J. Physiol. 246:R20–R25, (1984). Okada et al. (Am. J. Physiol., (1992), 272, p. R106) showed that mifepristone (RU486), a glucocorticoid receptor type II antagonist, reverses a dietary form of obesity. When Osbome-Mendel (OM) rats were placed on a high fat diet, they gained more weight and had larger retroperitoneal and parametrial fat pads than OM rats fed high-carbohydrate low fat diet. RU486 (30mg/kg-day) for 14 days completely reversed the body weight gain and the increase in fat pad size for the OM rats on the high fat diet. The authors suggested that the type II glucocorticoid receptor modulates body fat deposition and is essential for the development of obesity.

SUMMARY OF THE INVENTION

The present invention provides methods for treating mammals having type II Diabetes or one or more of the following symptoms of Type II Diabetes or Syndrome X: hyperglycemia; hyperinsulinemia; inadequate glucose clearance; obesity; hypertension, or high glucocorticoid levels by administering one or more agents exhibiting glucocorticoid receptor type I agonist and glucocorticoid receptor type II antagonist activities. Treatment agents of the present invention enhance circulating glucose clearance. A treatment may be implemented wherein two treatment compounds are administered in combination, one treatment compound having glucocorticoid receptor type I agonist activity, and a second treatment compound having glucocorticoid receptor type II antagonist activity. Alternatively, a single treatment agent of the present invention exhibits both glucocorticoid receptor type I agonist and glucocorticoid receptor type II antagonist activities. Suitable treatment agents, as well as therapeutic protocols and dosages for treating mammals are described below.

Screening assays for identifying agents having glucocorticoid receptor type I agonist activity and glucocorticoid receptor type II antagonist activity are also disclosed. Such screening assays preferably utilize recombinant techniques to screen steroid libraries, combinatorial chemistry libraries, natural and other compounds for the desired activities.

Bioassays for evaluating compounds having glucocorticoid receptor type I agonist activity and glucocorticoid receptor type II antagonist activity as potential treatment agents are also disclosed. Such bioassays preferably employ recombinant techniques.

DETAILED DESCRIPTION OF PREFERRED EMBODIMENTS

Treatment methods of the present invention are based upon the experimental studies described below. Diabetic, obese (ob/ob) mice, are well established murine models of Type II diabetes. In general, Type II diabetes in mice and humans is characterized by the same spectrum of symptoms. Murine steroids and human steroids are closely related, as are the murine and human steroid receptors and response patterns. One of ordinary skill in the art would thus expect treatment methods that are efficacious in murine models of Type II Diabetes, such as ob/ob mice, to be efficacious in humans. Similarly, one of ordinary skill in the art would expect treatment agents that are efficacious in murine models of Type II Diabetes, such as ob/ob mice, to be efficacious in humans.

In the examples described below, genetically obese (ob/ob) mice were treated experimentally with two different glucocorticoid receptor type I agonists: deoxycorticosterone and d-aldosterone; the glucocorticoid receptor type II antagonist mifepristone, referred to as "RU486;" and combinations of a glucocorticoid receptor type I agonist and type II antagonist, including combinations of RU486 with deoxycorticosterone and RU486 with d-aldosterone. Combined administration of a glucocorticoid type I agonist (deoxycorticosterone or d-aldosterone) with a glucocorticoid type II antagonist (RU486) resulted in a statistically significant enhancement of glucose clearance following a glucose challenge. The following examples provide a detailed description of the experimental protocols used and results obtained.

EXAMPLE I

This experiment measured the effects of administration of the following treatment agents: RU486, a glucocorticoid receptor type II antagonist; deoxycorticosterone, a glucocorticoid receptor type I agonist; d-aldosterone, a glucocorticoid receptor Type I agonist; and the combination of RU486 with deoxycorticosterone. These treatment agents were evaluated for their effects on body weight, glucose clearance, and glucocorticoid levels in female ob/ob mice.

Twenty-seven 3-month old ob/ob mice were adapted to single cages for one week prior to administration of the treatment agents. The mice were anesthetized with metofane, and bled for plasma and serum by retro-orbital draw between 10:45 a.m. and noon, at which time endogenous corticosterone levels are stable. Plasma was collected and plasma glucose levels were determined using a Kodak Ektachem DT 60 II system analyzer (referred to hereafter as "Kodak Ektachem"). Serum samples were stored at −80° C. for later determination of corticosterone levels, using a radioimmunoassay (RIA) kit purchased from ICN. The mice were then implanted subcutaneously in the lower right back area with 21 day treatment agent release pellets purchased from Innovative Research of America, Sarasota, Fla. The following pellets and sample sizes were used: Placebo (containing cholesterol, lactose, celluloses, phosphates and stearates) (25 mg/pellet, n=4); RU486 (25 mg/pellet, n=4); deoxycorticosterone (1.5 mg/pellet, n=4); RU486 +deoxycorticosterone (25 mg/pellet RU486, 1.5 m/pellet deoxycorticosterone, n=4); d-aldosterone (50 µg/pellet, n=3; 100 µg/pellet, n=3; and 250 µg/pellet, n=3). Multiple dosages of the candidate treatment agents, RU486, d-aldosterone and deoxycorticosterone, had been tested previously to determine effective dosages.

The mice were maintained under normal conditions and fed ad libitum for twenty days. Eighteen hours prior to the completion of the twenty-one day treatment, the mice were fasted. Following the eighteen hour fast, the mice were bled retro-orbitally and the baseline plasma glucose levels were determined by Kodak Ektachem analyzer. All groups were then challenged with 0.5 ml 25% glucose solution administered intraperitoneally. Blood was drawn retro-orbitally at 90, 210 and 300 minutes following the glucose challenge, and plasma glucose determinations were made by Kodak Ektachem analyzer.

Baseline fasting glucose appeared to be reduced in the d-aldosterone (100 μg) treatment group compared to the placebo group. No other treatment group demonstrated reduced fasting glucose at the end of the three week study. None of the treatment groups showed any appreciable effects on corticosterone levels. The RU486, RU486 and deoxycorticosterone and d-aldosterone (250 μg) treatment groups appeared to have reduced body weight gains compared to the placebo group, but body weight gains were not statistically different among the treatment and placebo groups. Table I, below, shows the baseline and post glucose challenge mean plasma glucose levels of the placebo and treatment groups.

TABLE I

| Treatment Group | PLASMA GLUCOSE (mg/dl) | | | |
|---|---|---|---|---|
| | Baseline (Mean) | 90 min. (mean) | 210 min. (mean) | 300 min. (mean) |
| placebo (n = 5) | 346.40 | 970.00 | 820.80 | 731.00 |
| Deoxy (n = 4) | 275.00 | 923.00 | 1047.00 | 783.50 |
| RU486 (n = 4) | 387.25 | 936.00 | 1213.00 | 1027.00 |
| RU486 & Deoxy (n = 4) | 345.25 | 669.00 | 552.00 | 389.00 |
| d-Aldo (50 μg) (n = 3) | 217.33 | 742.33 | 729.33 | 614.67 |
| d-Aldo (100 μg) (n = 3) | 203.33 | 758.00 | 704.00 | 520.00 |
| d-Aldo (250 μg) (n = 3) | 383.00 | 1335.00 | 1116.00 | 902.00 |

Plasma glucose levels in the placebo group were elevated approximately 2.8 fold at 90 minutes following glucose challenge; 2.4 fold at 210 minutes following glucose challenge; and 2.1 fold at 300 minutes following glucose challenge, all compared to the baseline glucose level. The RU486 +deoxycorticosterone treatment group demonstrated significantly lower increases in plasma glucose compared to the baseline level at all time points and, at 300 minutes following the glucose challenge, had nearly returned to baseline levels.

These results demonstrate that the combination of a type I glucocorticoid receptor agonist (deoxycorticosterone) with a type II glucocorticoid receptor antagonist (RU486) enhanced glucose clearance in ob/ob mice following a glucose challenge, at doses in which neither a type I glucocorticoid agonist nor a type II glucocorticoid antagonist alone produced any enhanced glucose clearance. The effect of deoxycortisone and RU486 on glucose clearance was not associated with reductions in body weight or circulating corticosterone levels, indicating that the beneficial effects on glucose clearance are not mediated by alterations in endogenous glucocorticoids or body weight.

EXAMPLE II

The methodology of this experiment was similar to that of Experiment I, above. The following treatment agents were used: RU486, a glucocorticoid type II antagonist; deoxycorticosterone, a glucocorticoid type I agonist; d-aldosterone, a glucocorticoid type I agonist; and the combinations of RU486 with deoxycorticosterone and RU486 with d-aldosterone. These treatment agents were evaluated for their effects on body weight, glucose metabolism and glucocorticoid levels in ob/ob mice.

Fifty-seven two month old female ob/ob mice were adapted to single cages for one week prior to administration of the treatment agents. The mice were separated into two groups, Group I and Group II. Treatment for each group followed the same procedure. Each group of mice was fasted for eighteen hours prior to initial blood draw and administration of the treatment or placebo pellet. For the blood draw, the mice were anesthetized with ether and blood was drawn by retro-orbital bleed. Plasma glucose and triglyceride levels were determined by Kodak Ektachem analyzer. Additional serum aliquots were stored at −80° C. for later determination of corticosterone levels by RIA. The mice were then grouped according to their plasma glucose levels, such that each group had a mean glucose level similar to the mean for the entire group.

The mice were then anesthetized with metofane, and implanted with the relevant pellet. Twenty-one day treatment agent release pellets were used, as described in Example I. Group I included the following treatment pellets and sample numbers: placebo (25 mg/pellet, n=5); RU486 (25 mg/pellet, n=5); deoxycorticosterone (1.5 mg/pellet, n=5); RU486 +deoxycorticosterone (25 mg/pellet RU486, 1.5 mg/pellet deoxycorticosterone, n=5); d-aldosterone (100 μg/pellet, n=3); and RU486 +d-aldosterone (25 mg/pellet RU486, 100 μg/pellet d-aldosterone, n=4). Group II included the following treatment pellets and sample numbers: placebo (25 mg/pellet, n=5); RU486 (25 mg/pellet, n=5); deoxycorticosterone (1.5 mg/pellet, n=5); RU486 +deoxycorticosterone (25 mg/pellet RU486, 1.5 mg/pellet deoxycorticosterone, n=8); d-aldosterone (100, μg/pellet, n=3); and RU486 +d-aldosterone (25 mg/pellet RU486, 100 μg/pellet d-aldosterone, n=4).

The mice were maintained under normal conditions and fed ad libitum for twenty days. Eighteen hours prior to the completion of the twenty-one day treatment, the mice were fasted. Following the eighteen hour fast, the mice were bled retro-orbitally, and the baseline plasma glucose levels were determined by Kodak Ektachem analyzer. The mice were then challenged with 0.5 ml 25% glucose solution administered intraperitoneally. Blood was drawn retro-orbitally at 90, 180 and 270 minutes, and at 20 hours post glucose challenge, and plasma glucose determinations made by Kodak Ektachem analyzer. Two mice in the Group I placebo group died prior to the 20 hour post glucose challenge time point; one mouse in each of the Group I d-aldosterone, RU486 and deoxycorticosterone treatment groups died prior to the 20 hour post glucose challenge time point; and one mouse in the Group I RU486 +d-aldosterone treatment group died prior to the 90 minute post glucose challenge time point. Three mice in the Group II placebo group died prior to the 20 hour post glucose challenge time point; one mouse in each of the Group II RU486 +d-aldosterone and Group II RU486 treatment groups died prior to the 20 hour post glucose challenge time point; and two mice in the Group II RU486 +deoxycorticosterone treatment group died prior to the 90 minute post glucose challenge time point.

Only the d-aldosterone treatment group appeared to have a lower mean body weight gain over the treatment period compared to the placebo group. All other treatment groups appeared to demonstrate higher mean body weight gains. There was, however, no statistically significant difference between baseline body weights or body weight change among any of the groups. There was no difference among any of the groups in baseline triglyceride levels or the change in triglyceride levels over the course of the three week study. There also was no difference between baseline corticosterone levels or the change in corticosterone levels among any group compared to the placebo.

Baseline fasting glucose appeared to be reduced after the three week study in the RU486 and RU486 +d-aldosterone treatment groups compared to the placebo group, but the results were not statistically significant. Table II, below, shows the baseline and post glucose challenge plasma glucose levels for the Group I and Group II placebo and treatment groups combined.

TABLE II

| Treatment Group I | PLASMA GLUCOSE (mg/dl) | | | | |
|---|---|---|---|---|---|
| | Baseline (mean) | 90 min. (mean) | 180 min. (mean) | 270 min. (mean) | 20 hours (mean) |
| placebo | 352.7 | 1067.8 | 922 | 1103.2 | 670.2 |
| Deoxy-corticosterone | 341.9 | 940.8 | 846 | 884.3 | 692.3 |
| RU486 | 210.3 | 786.4 | 835.4 | 745.8 | 206.75 |
| RU486 & Deoxy Corticosterone | 291.9 | 809.5 | 746.7 | 649.3 | 384.3 |
| d-aldosterone | 398.5 | 933.3 | 910 | 862 | 416 |
| RU486 & d-aldosterone | 294.9 | 670.3 | 649.4 | 620.4 | 295.3 |

In response to the glucose challenge on day 21, the RU486 +deoxycorticosterone and RU486 +d-aldosterone combination treatment groups demonstrated statistically significantly reduced plasma glucose levels at 4.5 hours post challenge compared to the placebo group. Each of the agents alone produced no statistically significant effect. At the 3 hour post-glucose challenge time point, both combination treatment groups appeared to demonstrate reduced plasma glucose, but this result was not statistically significant.

At the 20 hour post glucose challenge time point, none of the treatment groups demonstrated statistically significant reductions in plasma glucose compared to the placebo group, using INSTAT and Bonferroni Multiple Comparisons Test. However, the RU486, RU486 +deoxycorticosterone, RU486 +d-aldosterone and d-aldosterone treatment groups appeared to have returned to pre-challenge levels, while the placebo and deoxycorticosterone groups continued to have elevated plasma glucose levels.

The combination of a glucocorticoid receptor type I agonist with a glucocorticoid receptor type II antagonist is more effective at normalizing post glucose challenge plasma glucose levels in ob/ob mice than either agent alone. These results appear to be independent of body weight, endogenous corticosterone and triglyceride levels.

The experimental results described above establish that a treatment regimen involving administration of a glucocorticoid receptor type I agonist in combination with a glucocorticoid receptor type II antagonist effectively reduces plasma glucose levels following a glucose challenge in diabetic, obese ob/ob mice. Based on these results and on the structural and functional attributes of known steroid compounds, one of ordinary skill in the art would also expect that a single treatment agent exhibiting both glucocorticoid receptor type I agonist and glucocorticoid receptor type II antagonist activity could be identified and/or synthesized and would effectively reduce plasma glucose levels. There is reason to believe that such a combination agent exists or could be successfully synthesized based on the fact that there are examples of steroid compounds that act as both steroid receptor agonists and antagonists. Steroid compounds having the desired activities, and methods for screening to identify compounds having both activities are described more fully below.

The glucocorticoid receptor type I agonists used experimentally, including deoxycorticosterone and d-aldosterone, are suitable for human administration. Other human or murine selective glucocorticoid receptor type I agonists would also be suitable, provided they do not induce clinically significant adverse side effects. The glucocorticoid receptor type II antagonist used experimentally in these studies, RU486, is not optimal as a treatment compound for administration to humans for Type II Diabetes as a regular course of treatment as a result of its progesterone antagonizing activities. Progesterone, similarly, is a glucocorticoid receptor type II antagonist, but may not be optimal as a result of its progesterone agonist activity. Additional treatment agents having glucocorticoid receptor type II antagonist activity that are suitable for use as human treatment agents may be identified using conventional screening techniques.

Preferred treatment agents of the present invention exhibit greater than 50% of full and, more preferably, full glucocorticoid receptor type II antagonist activity and/or partial glucocorticoid receptor type I agonist activity. Treatment agents exhibiting approximately 30% to 95% of the full glucocorticoid receptor type I agonist activity are preferred, with treatment agents exhibiting greater than 50% of the full glucocorticoid receptor type I agonist activity being especially preferred. The preferred glucocorticoid receptor type I agonist and glucocorticoid antagonist activities may be present in a single treatment agent, or in a combination of treatment agents.

Steroid derivatives having a combination of glucocorticoid receptor type I agonist activity and glucocorticoid receptor type II antagonist activity may be androgen-type steroid compounds. Such steroid compounds preferably comprise a double bond at the C16 position and an additional moiety at the C18 position. Treatment agents of the present invention exhibiting both glucocorticoid receptor type I agonist and type II antagonist activity preferably comprise the steroid structure shown below:

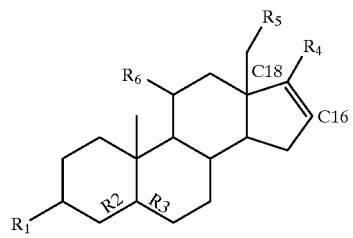

Wherein:
$R_1$ is any moiety, preferably O or OH;
$R_2$ is a single or double bond;
$R_3$ is single or double bond;
$R_4$ is any moiety, preferably $COCH_3$ or $COCH_2OH$;
$R_5$ is any moiety, preferably O or OH or, when $R_6$ is OH, $R_5$ is hemiacetal; and
$R_6$ is any moiety, preferably H or OH.

This steroid compound can be synthesized using synthesis techniques that are well known in the art. Suitable treatment agents according to the present invention may include moieties in addition to those disclosed above, provided the steroid compounds exhibit glucocorticoid receptor type I agonist activity and glucocorticoid receptor type II antagonist activity.

Suitable protocols, regimens and dosages for treatment of mammals using a combination of agents having glucocorticoid receptor type I agonist activity and glucocorticoid receptor type II antagonist activity can be extrapolated from the murine experimental data presented above, or can be independently determined based on variables such as individual Type II Diabetes or Syndrome X symptoms, including blood glucose levels, and the affinity and specificity of particular treatment agents. For example, a suitable human treatment protocol according to methods of the present invention may involve oral or intramuscular ("im") administration of a glucocorticoid receptor type II antagonist once daily (preferably in the morning or alternatively at bedtime) at a dosage level of from about 1.0 to 20 mg/kg/day, preferably from about 6 to about 12 mg/kg/day, in combination with oral or im administration of a glucocorticoid receptor type I agonist once daily (preferably in the morning or alternatively at bedtime) at a dosage level of from about 50 to 1000 µg/kg/day, preferably from about 200 to 800 µg/kg/day. A treatment agent exhibiting both type I agonist activity and glucocorticoid type II antagonist activity may be administered once daily, at a dosage level of from about 0.1 to 20 mg/kg/day, preferably at a dosage level of about 0.5 to 12 mg/kg/day.

Treatment agents of the present invention may alternatively be administered by implanting treatment agents release pellets, or by inhalation, transdermally, or using other means of administration. Effective dosages using alternative means of administration may be determined by one of ordinary skill in the art. Treatment according to the present invention may be monitored and adjusted by monitoring fasting glucose and circulating cortisol levels, with the objective of normalizing both fasting glucose and circulating cortisol levels.

Screening assays for identifying treatment agents exhibiting both glucocorticoid receptor type I agonist activity and glucocorticoid receptor type II antagonist activity are described in general terms below. Although general screening guidelines are set forth, it is recognized that one of ordinary skill in the art may design and implement numerous and diverse screening methodologies to identify treatment agents having the novel activities described herein. Screening assays preferably identify novel treatment agents exhibiting glucocorticoid receptor type I agonist activity at a level of approximately 30% to 95% full activity and glucocorticoid receptor type 1I antagonist activity at a level of greater than 50% full activity.

Both human and murine glucocorticoid receptors are well characterized, have been cloned, and are publicly available. Well known recombinant screening techniques and agents may be adapted to identify compounds exhibiting the desired glucocorticoid receptor antagonist and agonist activities. A two step screening process identifying compounds having glucocorticoid receptor type II antagonist activity first, and then screening those compounds for glucocorticoid receptor type I agonist activity is preferred. Compounds exhibiting both desired activities are then preferably screened for specificity using, for example, an androgen receptor such as estrogen receptor. Suitable treatment agents of the present invention preferably do not bind to an appreciable degree to other steroid receptors.

In an exemplary screening assay, well characterized cells, such as COS, CHO, BHK or the like, are transfected with a glucocorticoid type II receptor. Cells expressing the type II receptor are then transfected with a construct comprising a glucocorticoid response element linked to a reporter gene, such as a luciferase reporter gene. Many other types of reporter constructs are known and may be used. A baseline measurement of the extent of receptor binding to the response element may then be determined by means of a fluorescence assay. The cells are then incubated with potential treatment agent and receptor binding is again determined by fluorescence assay.

Agents that test positive for glucocorticoid receptor type II antagonist activity are then assayed for type I receptor agonist activity, using similar techniques. Finally, compounds exhibiting both glucocornicoid type I receptor agonism and type II receptor antagonism are screened for specificity. Specificity may be assessed, for example, by screening with an androgen receptor such as an estrogen receptor. Suitable treatment agents preferably do not agonize or antagonize other steroid receptors, such as estrogen receptors.

Alternatively, screening to identify treatment agents having the desired activities may be accomplished by assessing competitive binding to purified receptors. Receptors may be expressed in any suitable expression system, purified and plated. Competitive binding assays are then implemented using labeled compounds having known agonist and/or antagonist activities. Such techniques are well known in the art and it is well within the skill in the art to adapt such techniques for identifying treatment agents having the properties disclosed herein.

Candidate treatment agents are also preferably screened for specificity. Such a screen may be conducted using another steroid receptor, such as an androgen-type receptor, and preferably an estrogen receptor. Treatment agents exhibiting less than about 20% full agonist or antagonist activity with respect to another steroid receptor are deemed selective. Well known bioassay techniques for evaluating the suitability of candidate treatment agents for human therapeutic use may also be adapted to evaluate candidate treatment agents identified using the screening techniques described above.

I claim:

1. A method for treating a mammal having one or more symptoms of non-insulin-dependent Diabetes Mellitus comprising administering the following treatment agents, in combination:
   (a) a first treatment agent exhibiting glucocorticoid receptor type I agonist activity; and
   (b) a second treatment agent exhibiting glucocorticoid receptor type II antagonist activity.

2. A method according to claim 1, wherein the first and second treatment agents are administered orally or intramuscularly.

3. A method according to claim 1, wherein the second treatment agent is administered at a dosage of from about 1.0 to 20 mg/kg/day.

4. A method according to claim 3, wherein the second treatment agent is administered at a dosage of from about 6.0 to 12 mg/kg/day.

5. A method according to claim 1, wherein the first treatment agent is administered at a dosage of from about 50 to 1000 µg/kg/day.

6. A method according to claim 5, wherein the first treatment agent is administered at a dosage of from about 200 to 800 µg/kg/day.

7. A method according to claim 1, wherein the second treatment agent exhibits greater than 50% of full glucocorticoid receptor type II antagonist activity.

8. A method according to claim 1, wherein the first treatment agent exhibits approximately 30% to 95% of the full glucocorticoid receptor type I agonist activity.

9. A method for treating a mammal having one or more symptoms of non-insulin-dependent Diabetes Mellitus by administering a treatment agent exhibiting glucocorticoid receptor type I agonist activity and glucocorticoid receptor type II antagonist activity.

10. A method according to claim 9, wherein the treatment agent exhibits greater than 50% of full glucocorticoid receptor type II antagonist activity.

11. A method according to claim 9, wherein the treatment agent exhibits approximately 30% to 95% of the full glucocorticoid receptor type I agonist activity.

12. A method for reducing mammalian blood glucose levels comprising administering a treatment agent exhibiting glucocorticoid receptor type I agonist activity and glucocorticoid receptor type II antagonist activity.

13. A method for reducing mammalian blood glucose levels comprising administering the following treatment agents, in combination:
 (a) a first treatment agent exhibiting glucocorticoid receptor type I agonist activity; and
 (b) a second treatment agent exhibiting glucocorticoid receptor type II antagonist activity.

* * * * *